United States Patent [19]

Uchikawa et al.

[11] Patent Number: 4,773,376
[45] Date of Patent: Sep. 27, 1988

[54] OXYGEN GAS CONCENTRATION-DETECTING APPARATUS AND AIR-FUEL RATIO-CONTROLLING APPARATUS USING SAME IN INTERNAL COMBUSTION ENGINE

[75] Inventors: Akira Uchikawa; Satoshi Anbe; Masami Kawashima; Tatsumasa Yamada; Tadao Suwa, all of Isesaki, Japan

[73] Assignee: Japan Electronic Control Systems Co., Ltd., Gunma, Japan

[21] Appl. No.: 117,507

[22] Filed: Nov. 6, 1987

[30] Foreign Application Priority Data

| Nov. 10, 1986 | [JP] | Japan | 61-171348 |
| Dec. 3, 1986 | [JP] | Japan | 61-286779 |
| Jan. 30, 1987 | [JP] | Japan | 62-018558 |
| Feb. 3, 1987 | [JP] | Japan | 62-021840 |
| Mar. 24, 1987 | [JP] | Japan | 62-042058[U] |

[51] Int. Cl.⁴ .................................................. G01N 27/46
[52] U.S. Cl. ..................................... 123/489; 123/440; 204/406; 204/1 T
[58] Field of Search ............... 123/489, 440; 204/406, 204/1 T, 408, 412

[56] References Cited

U.S. PATENT DOCUMENTS

| 4,578,172 | 3/1986 | Yamada et al. | 123/489 |
| 4,610,741 | 9/1986 | Mace | 204/412 |
| 4,615,772 | 10/1986 | Hatrick | 204/1 T |
| 4,629,549 | 12/1986 | Kojima et al. | 204/412 |
| 4,642,174 | 2/1987 | Shibata | 204/408 |
| 4,664,773 | 5/1987 | Suzuki et al. | 204/406 |
| 4,707,241 | 11/1987 | Nakagawa et al. | 123/489 |
| 4,718,999 | 1/1988 | Suzuki et al. | 204/410 |

*Primary Examiner*—Raymond A. Nelli
*Attorney, Agent, or Firm*—Sandler & Greenblum

[57] ABSTRACT

Disclosed is an oxygen gas concentration-detecting apparatus comprising a ceramic substrate for generating an electromotive force according to oxygen gas concentration of gases contacted with both the surfaces of the ceramic substrate, a pair of electrode members arranged on the ceramic substrate to take out the electromotive force, an oxidation catalyst layer formed on the outer surface of the ceramic substrate to promote oxidation reaction of unburnt components and a reduction catalyst layer arranged on the outer surface of the ceramic substrate to promote reduction reaction of nitrogen oxides. By this apparatus, the concentration of oxygen gas inclusive of oxygen gas generated by reduction of nitrogen oxides can be precisely detected, and discharge of nitrogen dioxides is controlled and a so-called EGR control device can be omitted. When this oxygen gas concentration-detecting apparatus is applied to an air-fuel ratio feedback control apparatus in an internal combustion engine, the above-mentioned effects are enhanced.

21 Claims, 6 Drawing Sheets

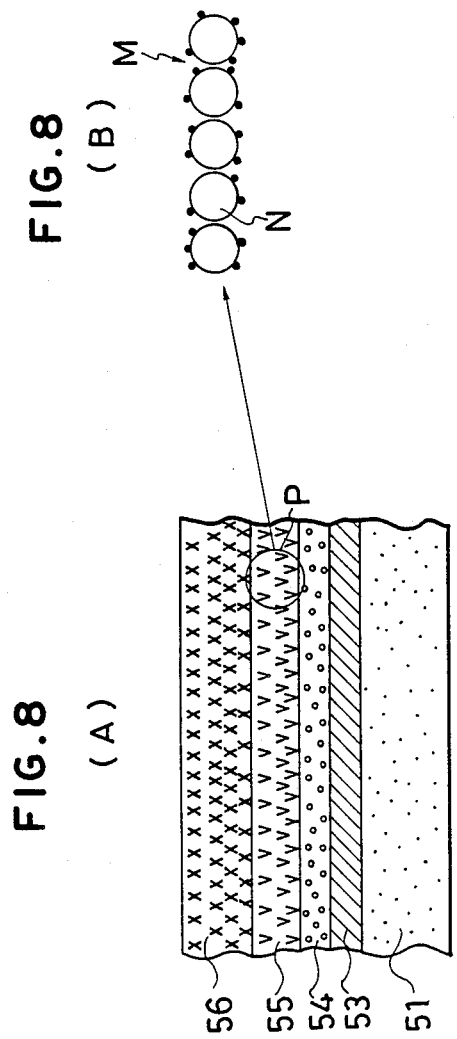

OXYGEN GAS CONCENTRATION-DETECTING APPARATUS AND AIR-FUEL RATIO-CONTROLLING APPARATUS USING SAME IN INTERNAL COMBUSTION ENGINE

BACKGROUND OF THE INVENTION

1. Field of the Invention

The present invention relates to an apparatus for detecting the oxygen gas concentration in a sample gas. More particularly, the present invention relates to an apparatus attached to an exhaust tube of an internal combustion engine, which is suitable for detection of the oxygen gas concentration in the exhaust gas, which has a close relation to the air-fuel ratio of an air-fuel mixture supplied to the engine. This oxygen gas concentration-detecting apparatus of the present invention can be preferably used as means for detecting the oxygen gas concentration in an exhaust gas from an external combustion engine or a manufacturing plant. Moreover, the present invention relates to an apparatus for measuring the oxygen gas concentration in an exhaust gas of an internal combustion engine by using the above-mentioned oxygen gas concentration-detecting apparatus and performing feedback control of the air-fuel ratio of the internal combustion engine.

2. Description of the Related Art

As means for detecting the oxygen gas concentration in an exhaust gas of an internal combustion engine (hereinafter referred to as "$O_2$ sensor"), an apparatus disclosed in Japanese Patent Application Laid-Open Specification No. 203828/84 is known, and the main part for detecting the oxygen gas concentration in the $O_2$ sensor is known, for example, from Japanese Patent Application Laid-Open Specification No. 204365/83 or Japanese Utility Model Application Laid-Open Specification No. 31054/84.

Namely, the main part of the $O_2$ sensor has a ceramic tube (ceramic substrate) having the top end portion closed as in a test tube and being composed mainly of zirconium oxide ($ZrO_2$), and parts of the inner and outer surfaces of the ceramic tube are coated with a platinum (Pt) paste and the ceramic tube is then calcined to form a pair of electrodes for taking out an electromotive force. Furthermore, platinum is vacuum-deposited on the outer surface of the ceramic tube to form an oxidation catalyst layer for oxidizing unburnt components in the exhaust gas, such as CO and HC. Then, a metal oxide such as magnesium spinel is flame-sprayed on the oxidation catalyst layer to form a protecting layer for protecting the oxidation catalyst layer.

In this structure, the air is introduced as the stable reference gas into the cavity of the ceramic tube, and the outer side of the ceramic tube is exposed to an exhaust gas passage of the engine and is contacted with the exhaust gas of the engine. A voltage corresponding to the ratio of the oxygen gas concentration in air contacted with the inner surface of the ceramic tube to the oxygen gas concentration in the exhaust gas contacted with the outer surface of the ceramic tube is generated between the pair of electrodes, and the oxygen gas concentration in the exhaust gas is detected based on this voltage.

It is considered that the electromotive force effect is generated between the electrodes on the inner and outer surfaces of the ceramic tube according to the following mechanism.

If calcia (CaO) or yttria ($Y_2O_3$) is added to zirconia ($ZrO_2$) known as the main component of a ceramic and the mixture is heated, calcia or yttria is included in the crystal and a lattic defect of the oxygen ion is formed, whereby zirconia is formed into a pure oxygen ion conductor in which the oxygen ion moves though either the electron or the hole hardly moves. If the oxygen partial pressure on one wall of densified zirconia is made different from the oxygen partial pressure on the other wall, it is only the oxygen ion $O^{2-}$ that can move, and as the result, an elecrtomotive force E represented by the following formula is generated according to the oxygen partial pressure ratio:

$$E=(RT/4F)ln(PI/PII)$$

wherein R stands for the gas constant, T stands for the absolute temperature, F stands for Faraday's constant, ln stands for the natural logarithm, and PI and PII stand for the oxygen partial pressures.

Incidentially, the oxidation catalyst layer of platinum promotes oxidation reactions of $CO+\frac{1}{2}O_2 \rightarrow CO_2$ and $HC+O_2 \rightarrow H_2O+CO_2$ between oxygen $O_2$ and carbon monoxide CO or hydrocarbon HC, and when combustion is carried out with an air-fuel mixture richer than the stoichiometric air-fuel ratio, CO or HC is conveniently reacted with low-concentration $O_2$ left in the air-fuel mixture to reduce the $O_2$ concentration almost to zero, whereby the $O_2$ concentration ratio between the inside and outside of the ceramic tube is increased and a large electromotive force is generated. On the other hand, when combustion is carried out with an air-fuel mixture leaner than stoichiometric air-fuel ratio, since high-concentration $O_2$ and low-concentration CO and HC are present in the exhaust gas, even if $O_2$ reacts with CO and HC, $O_2$ still remains in a considerable amount, and the $O_2$ concentration ratio between the inside and outside of the ceramic tube is low and no substantial voltage is produced.

Since the value of the electromotive force put out from the $O_2$ sensor abruptly changes in the vicinity of the stoichiometric air-fuel ratio as pointed out above, by utilizing this phenomenon, it is judged whether or not the air-fuel ratio in an air-fuel mixture sucked in the engine is the stoichiometric air-fuel ratio. If the air-fuel ratio is richer than the stoichiometric air-fuel ratio, the amount of the fuel to be supplied into the engine is decreased or the amount of the intake air is increased, and if the air-fuel mixture is leaner than the stoichiometric air-fuel ratio, the amount of the fuel is increased or the amount of the intake air is decreased. Thus, feedback control of the air-fuel ratio is performed.

Incidentally, in the above-mentioned conventional $O_2$ sensor, the oxidation catalyst layer has no substantial effect of reducing nitrogen oxides NOx, and therefore, the oxygen concentration in the exhaust gas is detected irrespectively of the concentration of nitrogen oxides $NO_2$.

Incidentally, nitrogen oxides NOx are formed by bonding of nitrogen $N_2$ in the air to oxygen $O_2$ is a high temperature atmosphere.

Namely, $O_2$ in NOx should be detected as $O_2$, which has not made any contribution to combustion, for detection of the air-fuel ratio, but this oxygen $O_2$ is not detected by the conventional $O_2$ sensor.

Accordingly, the detection value of the $O_2$ sensor is increased by the amount corresponding to the amount of oxygen which has reacted with nitrogen gas $N_2$ to form NOx, and in the air-fuel ratio region where the detection value of the $O_2$ sensor is inverted, the apparent air-fuel ratio is leaner than the actual air-fuel ratio.

Therefore, if feedback control of the air-fuel ratio is performed according to the detection result based on the air-fuel ratio in the inversion region of the $O_2$ sensor as the reference, the air-fuel ratio is erroneously controlled to a level leaner than the stoichiometric air-fuel ratio as the target air-fuel ratio, and there is a risk that oxidation reaction of nitrogen gas is advanced and nitrogen oxides NOx in the exhaust gas are excessive.

In general, a ternary catalyst for purging the exhaust gas, which is disposed in the exhaust gas passage in the engine, can simultaneously convert CO, HC and NOx efficiently when the air-fuel ratio is close to the stoichiometric air-fuel ratio, but if the air-fuel ratio is controlled to a level leaner than the stoichiometric air-fuel ratio, the conversion of NOx is abruptly reduced and the amount of NOx discharged to the air present downstream of the ternary catalyst passage is drastically increased.

According to the conventional technique, so-called exhaust gas recycle (EGR) control for reducing nitrogen oxides NOx by recycling a part of the exhaust gas of the engine into the intake air and thus lowering the combustion temperature. However, the structure of this EGR control system is complicated because an EGR passage should be laid out and an EGR control valve or the like should be disposed in this passage, and this results in increase of the cost. Moreover, the combustion efficiency is reduced by introduction of the exhaust gas and the fuel expense is greatly increased.

Accordingly, if feedback control of the air-fuel ratio of the internal combustion engine is performed by the conventional inaccurate $O_2$ sensor, excessive discharge of nitrogen oxides NOx cannot be avoided, and in order to prevent nitrogen oxides NOx from being discharged to the outside, the EGR control system should be disposed in the internal combustion engine, which inevitably resides in the above-mentioned disadvantages.

SUMMARY OF THE INVENTION

It is therefore a primary object of the present invention to provide an oxygen gas concentration-detecting apparatus in which reaction of nitrogen oxides NOx is further promoted to eliminate the above-mentioned disadvantages of the conventional $O_2$ sensor structure and the concentration of oxygen, exclusive of oxygen gas which has not participated in combustion, for example, oxygen gas in $CO_2$, in a sample gas can be detected more accurately.

Another object of the present invention is to provide an air-fuel ratio-controlling apparatus in which feedback control of the air-fuel ratio of an internal combustion engine is performed by using the above-mentioned improved oxygen gas concentration-detecting apparatus to obtain an air-fuel ratio much closer to the aimed air-fuel ratio.

According to the present invention, in order to attain the foregoing objects, an oxidation catalyst layer for promoting oxidation reaction and a reduction catalyst layer for promoting reduction reaction of nitrogen oxides NOx are formed on the surface of a ceramic substrate having a pair of electrodes arranged on both the surfaces thereof to generate an electromotive force corresponding to the concentration of oxygen gas $O_2$ between the eletrodes.

According to the oxygen gas concentration-detecting apparatus of the present invention, since reduction reaction of nitrogen oxide NOx is promoted by the reduction catalyst layer, the oxygen gas concentration on the second surface side of the ceramic substrate is increased by this reduction reaction. Therefore, the difference between the $O_2$ concentration on the open air side and the oxygen gas concentration on the exhaust gas side is proportionally decreased, and the electromotive force of the oxygen gas concentration-detecting apparatus is reduced and a richer value than in the conventional apparatus is detected. Therefore, as the concentration of nitrogen oxides NOx is high, the air-fuel ratio is detected on the rich side and if feedback control of the air-fuel ratio is performed based on this detection result, the air-fuel ratio is controlled to a rich stoichiometric air-fuel ratio. Since it is known that nitrogen oxides NOx are more frequently formed at an air-fuel ratio leaner than the stoichiometric air-fuel ratio, control of the air-fuel ratio to the rich side, as in the present invention, makes contributions to decrease of nitrogen oxides NOx.

According to the present invention, it has been found that a ceramic containing platinum Pt is preferred for the oxidation catalyst layer. It has also been found that a ceramic having rhodium Rh or ruthenium Ru incorporated therein is preferred for the reduction catalyst layer and if titanium oxide $TiO_2$ or lanthanum oxide $La_2O_3$ is used as the carrier, the conversion of nitrogen oxides NOx to $N_2$ is higher than in case of other carriers and reduction by rhodium Rh or ruthenium Ru is performed most efficiently.

The reduction catalyst layer can also be formed by supporting particles of a reduction catalyst for promoting reduction reaction of nitrogen oxides NOx on cerium oxide and incorporating the particles in a porous layer.

The oxidation catalyst layer and reduction catalyst layer are laminated on the second surface of the ceramic substrate, and it is preferred that the vertical positional relationship between the two layers be such that the reduction catalyst layer is an upper layer. An air-permeable protecting layer can be formed on the outer surface of the oxidation catalyst layer or reduction catalyst layer to prevent peeling of both the catalyst layers and adhesion of impurities such as carbon.

The ceramic substrate may be heated by a heater to activate generation of the electromotive force.

If the oxygen gas concentration-detecting apparatus of the present invention is used in combination with the conventional known air-fuel ratio feedback control means for an internal combustion engine, decrease of generation of NOx is precisely attained and a high control accuracy can be maintained.

The present invention will now be described in detail with reference to optimum embodiments illustrated in the accompanying drawings, but the present invention is not limited by these embodiments and the present invention includes changes and modifications within the range of the objects and the technical scope of the present invention.

BRIEF DESCRIPTION OF THE DRAWINGS

FIG. 8 is an enlarged view illustrating a fourth embodiment of the detecting zone of the oxygen gas concentration-detecting apparatus of the present invention, in which (A) is an enlarged sectional partial view of the detecting zone and (B) is an enlarged view of the region P in (A).

DETAILED DESCRIPTION OF THE PREFERRED EMBODIMENTS

Figure 1:
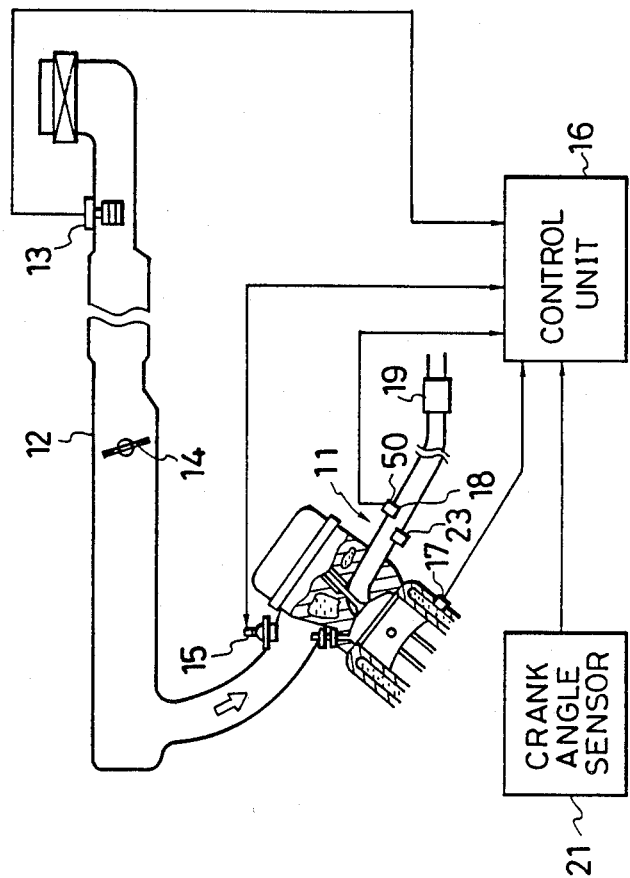
FIG. 1 is a systematic diagram of an air-fuel ratio control apparatus for an internal combustion engine, which is provided with the oxygen gas concentration-detecting apparatus of the present invention.

FIG. 1 illustrates an embodiment of an apparatus for controlling the air-fuel ratio of an internal combustion engine by using an oxygen gas concentration-detecting apparatus ($O_2$ sensor) of the present invention.

Referring to FIG. 1, an air flow meter 13 for detecting the intake air quantity Q and a throttle valve 14 linked with an accelerator pedal to control the intake air quantity Q are disposed in an intake passage 12 of an engine 11, and electromagnetic fuel injection valves 15 for respective cylinders are arranged in a manihold zone downstream of the intake passage 12. The fuel injection valve 15 is driven and opened by an injection pulse signal from a control unit 16 having a microcomputer built therein, and a fuel fed under compression from a fuel pump not shown in the drawings and controlled to a predetermined pressure by a pressure regulator is injected and supplied.

A water temperature sensor 17 is arranged to detect the cooling water temperature Tw in a cooling jacket in the engine 11. An $O_2$ sensor 30 (see FIGS. 1 and 2 with reference to the structure of the sensor zone) for detecting the air-fuel ratio of the sucked air-fuel mixture by detecting the oxygen gas concentration in the exhaust gas is arranged in an exhaust gas passage 18 so that an electromotive force-generating zone of the $O_2$ sensor is brought into contact with the exhaust gas. A ternary catalyst device 19 for effecting purging by oxidizing CO and HC in the exhaust gas and reducing NOx is arranged on the downstream side of the exhaust gas passage 18. A crank angle sensor 21 is built in a distributor not shown in the drawings, and crank unit angle signals put out from the crank angle sensor 21 synchronously with rotation of the engine are counted for a predetermined time in the control unit 16 or the synchronism of crank reference angle signals is measured, whereby the engine rotation number N is detected. An exhaust gas temperature sensor 23 for detecting the exhaust gas temperature is arranged in the exhaust gas passage 18.

Figure 2:
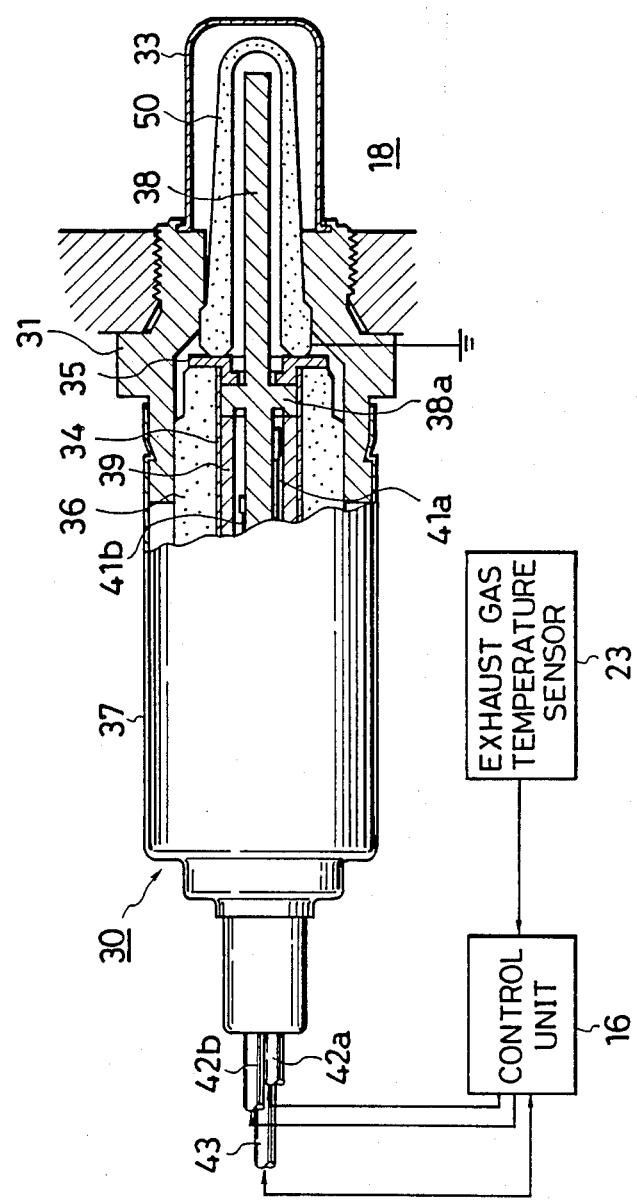
FIG. 2 is a partially cut-out side view of the oxygen gas concentration-detecting apparatus of the present invention, which mainly shows the detecting zone of the apparatus.

The structure of the $O_2$ sensor 30 is shown in FIG. 2. Referring to FIG. 2, an electromotive force-generating zone of oxygen gas concentration-detecting zone (hereinafter referred to as "detecting zone") 50 composed of a ceramic substrate and having a shape resembling the shape of a test tube is held on the top end portion of a holder 31 screwed through the wall portion of the exhaust passage 18 and the outer surface of the detecting zone 50 is exposed to the exhaust gas. The outer portion of the top end of the detecting zone 50 is covered with a slitted protector 33 to protect the top end of the detecting zone 50 from an external force. A contact plate 35 formed of a metal and attached to the top end of a cylindrical heater case 34 is brought into contact with the base end portion of the detecting zone 50. The top end of an isolation bush 36 covering the heater case 34 is pressed to the contact plate 35 and fitted in the inner circumferential surface of the base end portion of the holder 31. One end of a cap 37 having a substantially cylindrical shape is caulked and fixed to the outer circumferential surface of the base end portion of the holder 31.

A rod-shaped heater 38 composed of alumina is inserted into the heater case 34, and a flange 10a formed integrally in the intermediate portion of the heater 38 is pressed and secured to the contact plate 35. The top end of the heater 38 pierces through the contact plate 35 and extends to the interior space of the detecting zone 50. In the heater case 34, an isolation pipe 39 is inserted to surround the heater 38, and the top end of the isolation pipe 39 is pressed to a flange 38a.

Lead lines 41a and 41b for the heater 38 are connected to a pair of lead line harnesses 42a and 42b through a terminal not shown in the drawings and are connected to the control unit 16. By the control unit 16, the temperature of the heater 38 is controlled according to the exhaust gas temperature value detected by the exhaust gas temperature sensor 23.

A pair of electrodes described hereinafter are arranged in the detecting zone 50, and the outer electrode is earthed and the inner electrode is connected to a lead harness 43 for the sensor through the contact plate 35 and then to the control unit 16. The $O_2$ sensor 30 is disclosed in detail in Japanese Utility Model Laid-Open specification No. 118950/85.

The detecting zone 50 as the main part of the $O_2$ sensor 30 will now be described in detail.

Figure 3:
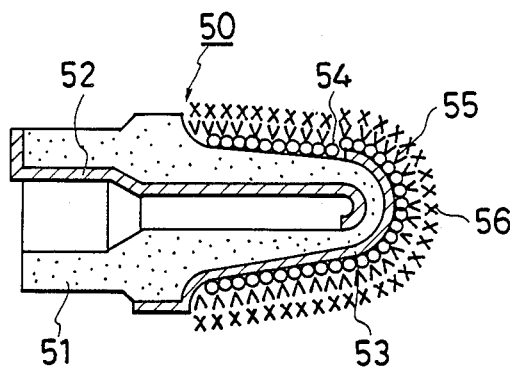
FIG. 3 is a sectional view diagrammatically illustrating the detecting zone of the oxygen gas concentration-detecting apparatus shown in FIG. 2.

Referring to FIG. 3, inner and outer electrodes 52 and 53 composed of platinum are formed at parts of the inner and outer surfaces of a ceramic substrate 51 having a shape resembling the shape of a test tube and having a closed top end portion composed mainly of zirconium oxide ($ZrO_2$). Platinum is vacuum-deposited on the outer surface of the ceramic substrate 51 to form an oxidation catalyst layer 54.

A reduction catalyst layer 55 of a ceramic comprising particles of rhodium Rh incorporated in γ-alumina having a large specific surface area is formed on the outer surface of the oxidation catalyst layer 54. The particles of rhodium Rh as the catalyst for promoting reduction reaction of nitrogen oxides NOx are incorporated (for example, 1 to 10%) in the carrier. The thickness of the reduction catalyst layer 55 is, for example, 0.1 to 5 μm. An air-permeable metal oxide such as magnesium spinel is flame-sprayed on the outer surface of the reduction catalyst layer 55 to form a protecting layer 56 for protecting the oxidation catalyst layer 54 and reduction catalyst layer 55 from an external force and preventing peeling of the layers 54 and 55 by deposition of carbon in the exhaust gas between the two layers 54 and 55.

Figure 4:
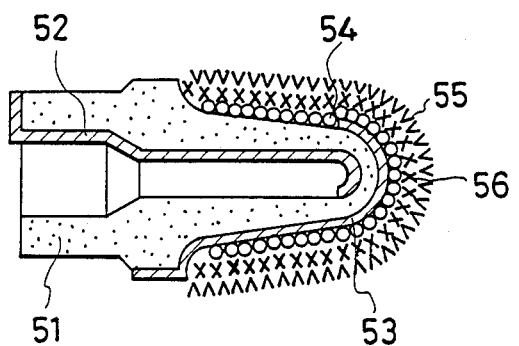
FIG. 4 is a diagrammatic sectional view showing a modification of the detecting zone of the oxygen gas concentration-detecting apparatus shown in FIG. 3.

Incidentally, the protecting layer 56 may be formed between the oxidation catalyst layer 54 and reduction catalyst layer 55, as shown in FIG. 4, or the protecting layer 56 need not be particularly formed.

Furthermore, ruthenium Ru can be used instead of rhodium Rh, and it is generally known that these components are effective as the reduction catalyst for nitrogen oxides NOx. If titanium oxide $TiO_2$ or lanthanum oxide $La_2O_3$ is used for the carrier of the reduction catalyst layer, reduction reaction of NOx can be performed very efficiently, as compared with the case where γ-alumina or the like is used. This has been confirmed by the experimental results shown in Table 1.

TABLE 1

| Carrier of Rh | Conversions of Nitrogen Oxides NOx | | |
|---|---|---|---|
| | Conversion (%) to NO | Conversion (%) to $N_2O$ | Conversion (%) to $N_2$ |
| $SiO_2$ | 11 | 38 | 51 |
| $Al_2O$ | 28 | 17 | 56 |
| MgO | 28 | 17 | 55 |
| $TiO_2$ | 5 | 22 | 73 |
| $La_2O_3$ | 6 | 21 | 70 |

Incidentally, the Rh content was the same in all of the runs shown in Table 1.

Namely, when titanium oxide $TiO_2$ or lanthanum oxide $La_2O_3$ is used as the carrier, the conversion to $N_2$ is much higher than in case of other carriers, and a largest amount of oxygen can be taken out from the same amount of nitrogen oxide NOx.

In the above-mentioned structure, when nitrogen oxides NOx contained in the exhaust gas arrive at the reduction catalyst layer 55 of the detecting zone 55, the reduction catalyst layer 55 promotes the following reactions of NOx with unburnt components CO and HC in the exhaust gas:

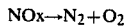

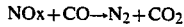

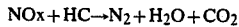

As the result, in the oxidation catalyst layer 54 located on the inner side of the reduction catalyst layer 55, since the amounts of unburnt components CO and HC are reduced by the reaction in the reduction catalyst layer 55, the $O_2$ concentration is proportionally increased. In short, the $O_2$ concentration is increased by the amount corresponding to $O_2$ generated in the reduction catalyst layer 55.

Figure 5:
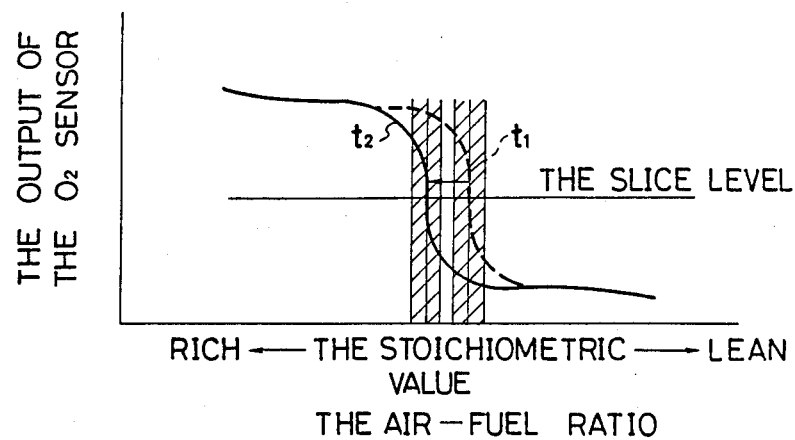
FIG. 5 is a graph comparing the oxygen gas concentration-detecting apparatus of the present invention with the conventional oxygen gas concentration-detecting apparatus with respect to the detection electromotive force, especially the air-fuel ratio at the time of inversion.

Accordingly, the difference between the $O_2$ concentration on the inner side of the ceramic substrate 51 falling in contact with the air and the $O_2$ concentration on the outer side falling in contact with the exhaust gas is decreased and the electromotive force of the $O_2$ sensor 30 is small, and as shown in FIG. 5, the air-fuel ratio region t1 at the time of inversion of the electromotive force is on the leaner side but in the air-fuel ratio region t2, at the time of inversion of the output value of the $O_2$ sensor 30 of the present invention, the detected air-fuel value is equal to or much closer to the stichiometric air-fuel ratio (λ=1) than the value detected by the conventional $O_2$ sensor incapable of detecting the concentration of oxygen gas contained in NOx. As the result, in the vicinity of the more accurate stoichiometric value, the electromotive force of the $O_2$ sensor is reduced below the slice level and accurate detection of the stoichiometric air-fuel ratio can be performed.

Figure 6:
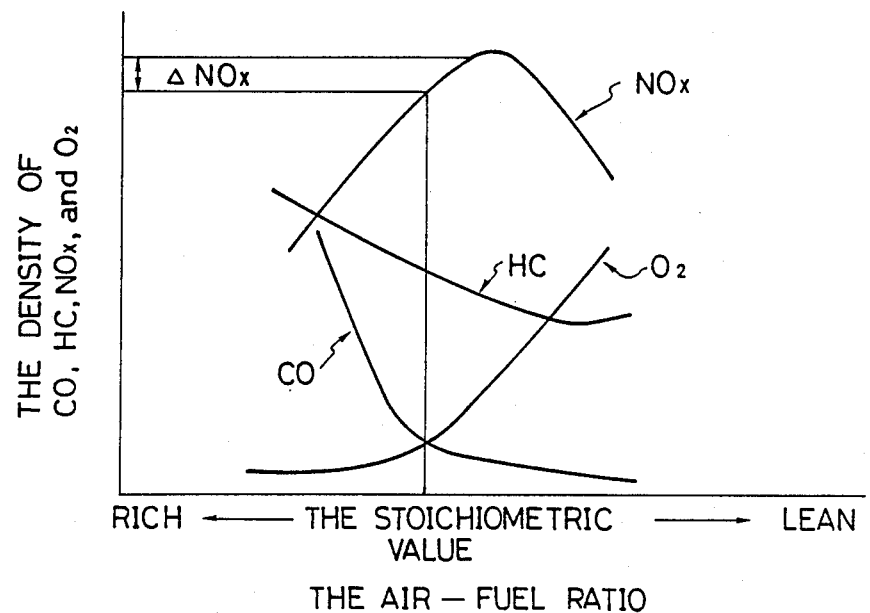
FIG. 6 is a graph showing the generation concentrations of unburnt components CO and HC, nitrogen oxides NOx and oxygen gas $O_2$, corresponding to the air-fuel ratio.

Therefore, if feedback control of the air-fuel ratio is carried out based on the detection result of the $O_2$ sensor (rich-lean judgement of the sucked air-fuel mixture), as shown in FIG. 6, the air-fuel ratio is equal or closer to the stoichiometric air-fuel ratio than the lean air-fuel ratio detected in the conventional $O_2$ sensor, and increase of the amount discharged of NOx is controlled by ΔNOx by the above-mentioned air-fuel ratio control.

Figure 7:
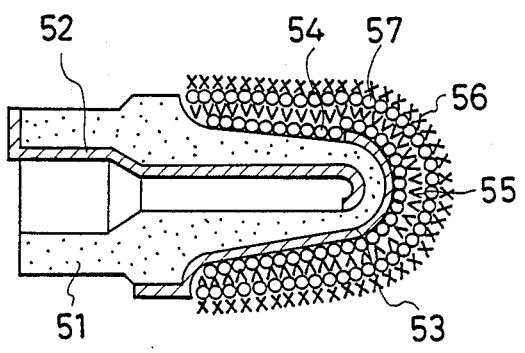
FIG. 7 is a diagrammatic sectional view illustrating a third embodiment of the detecting zone of the oxygen gas concentration-detecting apparatus of the present invention.

Furthermore, according to the present invention, there may be adopted a method in which, as shown in FIG. 7, a second oxidation catalyst layer 57 (which may be a platinum catalyst layer or a porous ceramic layer comprising platinum particles incorporated into a carrier of γ-alumina or the like) is formed on the outer surface of the reduction catalyst layer 55, unburnt components CO and HC are reacted with $O_2$ in this second oxidation catalyst layer 57, NOx is then reduced in the reduction catalyst layer 55 and the $O_2$ concentration is increased by reduction of NOx (NOx→$N_2O_2$). Namely, by reacting $O_2$ with CO and HC in the exhaust gas in the outermost second oxidation catalyst layer 57, $O_2$ obtained by reduction of NOx directly increases the concentration of oxygen $O_2$ on the outer surface side of the ceramic substrate 1. The first oxidation catalyst layer 54 performs oxidation reaction of unburnt components CO and HC, which may probably be left, more completely, resulting in increase of the accuracy of the $O_2$ sensor.

In the oxygen gas concentration-detecting apparatus shown in FIGS. 3, 4 and 7, in the case where rhodium Rh or ruthenium Ru is supported on alumina $Al_2O_3$, titanium oxide $TiO_2$ or lanthanum oxide $La_2O_3$ as the carrier, the specific surface area of the carrier is decreased under high temperature conditions and it is apprehended that the effect of the catalyst will not be sufficiently exerted. In this case, if catalyst particles of rhodium Rh or ruthenium Ru are supported on cerium oxide $CeO_2$ having a high shaped stability even under high temperature conditions, the specific surface area can be maintained even under high temperature conditions and the effect of the catalyst can be sufficiently exerted. If the reduction catalyst layer 55 is formed only of cerium oxide $CeO_2$ having catalyst particles of rhodium Rh or ruthenium Ru supported thereon, since the particle size of cerium oxide $CeO_2$ is small, circulation of the exhaust gas is inhibited when the reduction catalyst layer 55 is excessively densified. Therefore, in order to maintain circulation of the exhaust gas, it is preferred that cerium oxide $CeO_2$ be incorporated in a porous layer composed of alumina or the like. For example, as shown in FIGS. 8-(A) and 8-(B), a reduction catalyst layer 55 formed by incorporating a product M obtained by supporting particles of a reduction catalyst for promoting reduction reaction of nitrogen oxides NOx, such as rhodium Rh or ruthenium Ru, on cerium oxide $CeO_2$ (the Rh or Ru content in $CeO_2$ is 0.5 to 10% by weight) into a porous material N such as alumina $Al_2O_3$, titanium oxide $TiO_2$ or lanthanum oxide $La_2O_3$ (the $CeO_2$ content in the porous material is 20 to 50% by weight) exerts a desirable effect.

The above-mentioned reaction on the reduction catalyst layer 55 is advantageously advanced when the temperature of the reduction catalyst layer 55 is higher than 400° C., and if the temperature is lower and in the range of from 200° to 400° C., the following reaction is promoted and $NH_3$ is formed, and no good results can be obtained:

$$NOx + 5H_2 \rightarrow 2NH_3 + 2H_2O$$

At a temperature higher than 600 C., formed $NH_3$ causes reaction again and $H_2O$ or $N_2O$ is formed.

Accordingly, the exhaust gas temperature is detected by the exhaust gas temperature sensor 23, and the quantity of electricity applied to the ceramic heater 38 is controlled by the control unit 16 or a heater-controlling device disposed independently according to the detected exhaust gas temperature, so that the detecting zone 50 is maintained at 400° to 600° C.

If this structure is adopted, a certain NOx-detecting function can always be exerted irrespectively of the exhaust gas temperature.

Figure 9:
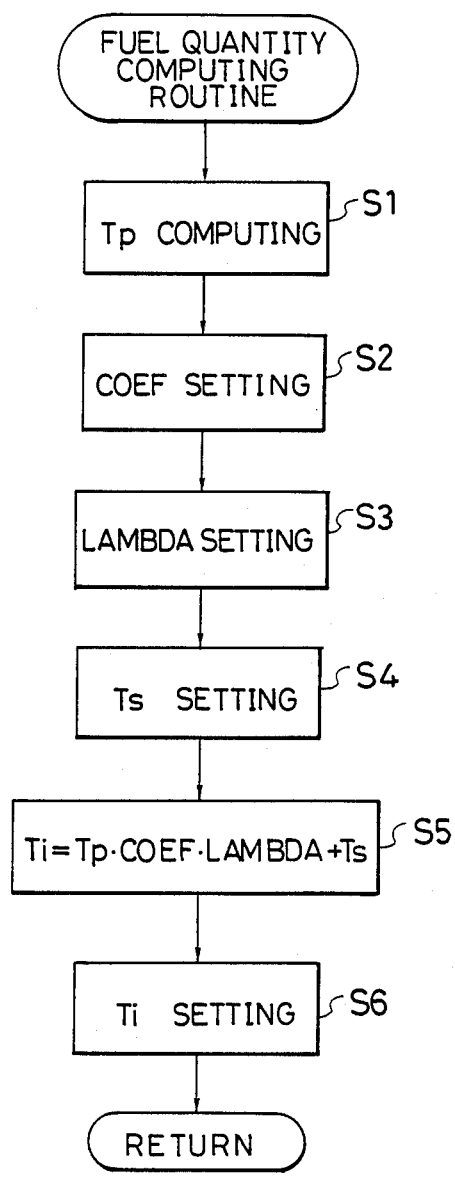
FIG. 9 is a flow chart showing the routine of computation of the fuel injection quantity by a control unit in performing feedback control of an internal combustion engine by using the oxygen gas concentration-detecting apparatus of the present invention.

The routine of computation of the fuel injection quantity by the control unit 16 will now be described with reference to the flow chart shown in FIG. 9.

Incidentally, since the air-fuel ratio is feedback-controlled by the fuel injection quantity computed based on the detection value of the $O_2$ sensor 30 according to this routine, this routine constitutes the feedback control means together with fuel injection valves and various sensors.

At step (S in FIG. 9) 1, the basic fuel injection quantity Tp corresponding to the flow quantity of intake air per unit rotation is computed based on the intake air flow quantity Q detected by the air flow meter 13 and the engine rotation number N calculated from signals from the crank angle sensor 21 according to the following equation:

$$Tp = K \cdot Q/N$$

wherein K is a constant.

At step 2, various correction coefficients COEF are set based on the cooling water temperature Tw detected by the water temperature sensor 17 and other factors.

At step 3, the feedback correction coefficient LAMBDA is set in the following manner based on signals from the $O_2$ sensor.

Namely, the output voltage Voz of the $O_2$ sensor 30 is read and compared with the slice level voltage Vref to judge whether the air-fuel ratio is rich or lean.

In the case where the air fuel ratio is lean (rich), it is judged whether or not the air-fuel ratio is at the time of inversion (inversion diameter) of the rich (lean) air-fuel ratio to the lean (rich) air-fuel ratio, and at the time of inversion, the feedback correction coefficient LAMBDA is increased (decreased) by a predetermined proportional constant P from the preceding value. At the time other than the time of inversion, the feedback correction coefficient LAMBDA is increased (decreased) by a predetermined integrative constant I from the preceding value. Thus, the feedback correction coefficient LAMBDA is increased (decreased) at a certain gradient. Incidentally, the relation of $P << I$ is established.

At step 4, the voltage correction value Ts is set based on the voltage value of the battery. This operation is performed to correct the change of the fuel injection quantity by the change of the battery voltage.

At step 5, the fuel injection quantity Ti is computed according to the following equation:

$$Ti = Tp \text{ COEF LAMBDA} + Ts$$

At step 6, computed Ti is set in an output register.

Thus, if a fuel injection timing of a predetermined engine rotation frequency is obtained, a driving pulse signal having a pulse width of Ti is given to the fuel injection valve 5 to effect injection of the fuel.

In this air-fuel ratio feedback control, the air-fuel ratio is periodically changed according to the change of the feedback correction coefficient LAMBDA, and in this case, the control center value is the value at the time of inversion of the electromotive force of the $O_2$ sensor.

Accordingly, if the above-mentioned air-fuel ratio feedback control is thus carried out based on the detection result of the $O_2$ sensor, the higher is the NOx concentration, to the richer value the air-fuel ratio is controlled.

Therefore, as shown in FIGS. 5 and 6, as the amount generated of NOx is increased, by controlling the air-fuel ratio to a richer level, the amount discharged of NOx can be efficiently decreased.

Furthermore, since the air-fuel ratio is made richer and the control is performed at an air-fuel ratio close to the true theoretical air-fuel ratio, the conversion of NOx by the ternary catalyst device 19 is increased and the amount of NOx discharged in the air can be drastically reduced. In addition, since the conversions of CO and HC can be maintained at high levels if the air-fuel ratio is close to the theoretical air-fuel ratio, increase of the amount of CO and HC discharged can be avoided.

Therefore, according to this control system, the EGR device which is necessary for decreasing NOx in the conventional apparatus need not be used and the cost can be greatly reduced. Moreover, large reduction of the fuel efficiency as caused by the EGR control is not caused at all, and since the air-fuel ratio is made rich (close to the stoichiometric value) in proportion to the NOx concentration, the fuel cost can be decreased.

Incidentally, the air-fuel control may always be carried out according to the NOx concentration in the air-fuel ratio feedback control as in the present embodiment. Alternatively, there can be adopted a method in which the driving region where reduction of NOx is intended is set based on the engine rotation number, the load and the like, the above-mentioned air-fuel ratio feedback control is conducted in this region according to the NOx concentration, this control is stopped in other regions, and in the air-fuel ratio feedback control, the air-fuel ratio is controlled to the theoretical air-fuel ratio by using the conventional $O_2$ sensor not including the reduction catalyst layer.

We claim:

1. An oxygen concentration-detecting apparatus comprising a ceramic substrate for generating an electromotive force between a first surface contacted with a reference gas and a second surface contacted with a gas to be detected according to the ratio of the concentration of oxygen gas $O_2$ between said two gases, a pair of electrode members formed at parts of said first and second surfaces, respectively, of said ceramic substrate, to take out said electromotive force as a detection signal, an oxidation catalyst layer arranged to cover the outer surface of said ceramic substrate and promote oxidation reaction of unburnt components, and a reduction catalyst layer arranged to cover an outer surface of said ceramic substrate and promote mainly reduction reaction of nitrogen oxides NOx.

2. An oxygen gas concentration-detecting apparatus as set forth in claim 1, wherein said ceramic substrate is constructed by incorporating a small amount of yttria $Y_2O_3$ or calcia CaO into zirconia $ZrO_2$ and calcining the mixture.

3. An oxygen gas concentration-detecting apparatus as set forth in claim 1, wherein said ceramic substrate has a shape resembling the shape of a test tube.

4. An oxygen gas concentration-detecting apparatus as set forth in claim 1, wherein said reference gas is the air and said gas to be detected is an exhaust gas of an internal combustion engine.

5. An oxygen gas concentration-detecting apparatus as set forth in claim 1, wherein said ceramic substrate has a shape resembling the shape of a test tube, said first surface is an inner surface of the ceramic substrate, and said second surface is an outer surface of said ceramic substrate.

6. An oxygen gas concentration-detecting apparatus as set forth in claim 1, wherein said oxidation catalyst layer is an oxidation catalyst layer containing platinum Pt.

7. An oxygen gas concentration-detecting apparatus as set forth in claim 1, wherein said reduction catalyst layer is a reduction catalyst layer having rhodium Rh or ruthenium Ru incorporated therein.

8. An oxygen gas concentration-detecting apparatus as set forth in claim 1, wherein said reduction catalyst layer comprises a carrier of titanium oxide $TiO_2$ and rhodium Rh or ruthenium Ru incorporated in the carrier.

9. An oxygen gas concentration-detecting apparatus as set forth in claim 1, wherein said reduction catalyst layer comprises a carrier of lanthanum oxide $La_2O_3$ and rhodium Rh or ruthenium Ru incorporated in the carrier.

10. An oxygen gas concentration-detecting apparatus as set forth in claim 1, wherein said reduction catalyst layer is constructed by supporting particles of a reduction catalyst for promoting reduction reaction of nitrogen oxides NOx on cerium oxide and incorporating the supported particles in a porous layer.

11. An oxygen gas concentration-detecting apparatus as set forth in claim 1, wherein said oxidation catalyst layer is formed on said second surface of said ceramic substrate and said reduction catalyst layer is formed on an outer surface of said oxidation catalyst layer.

12. An oxygen gas concentration-detecting apparatus as set forth in claim 11, which further comprises a second oxidation catalyst formed on an outer surface of said reduction catalyst layer.

13. An oxygen gas concentration-detecting apparatus as set forth in claim 11, wherein said reduction catalyst layer has on the outer surface thereof an air-permeable protecting layer.

14. An oxygen gas concentration-detecting apparatus as set forth in claim 11, wherein said reduction catalyst layer has on the outer surface thereof an air-permeable protecting layer capable of filtering solid impurities such as carbon.

15. An oxygen gas concentration-detecting apparatus as set forth in claim 11, wherein said oxidation catalyst layer has on the outer surface thereof an air-permeable protecting layer.

16. An oxygen gas concentration-detecting apparatus as set forth in claim 1, which further comprises a heater for heating the ceramic substrate.

17. An oxygen gas concentration-detecting apparatus as set forth in claim 16, which further comprises heater-controlling means for controlling the heating temperature of said heater.

18. An oxygen gas concentration-detecting apparatus as set forth in claim 1, which further comprises judging means for judging the concentration of oxygen gas $O_2$ in the gas to be detected according to the output value of the electromotive force generated between the pair of said electrode members.

19. An air-fuel ratio-controlling apparatus in an internal combustion engine, which comprises an oxygen gas concentration-detecting apparatus including a ceramic substrate for generating an electromotive force between a first surface contacted with a reference gas and a second surface contacted with an exhaust gas of the internal combustion engine according to the ratio of the concentration of oxygen gas $O_2$ between said two gases, a pair of electrode members formed at parts of said first and second surfaces, respectively, of said ceramic substrate, to take out said electromotive force as a detection signal, an oxidation catalyst layer arranged to cover an outer surface of said ceramic substrate and promote oxidation reaction of unburnt components, a reduction catalyst layer arranged to cover said outer surface of said ceramic substrate and promote reduction reaction of nitrogen oxides NOx, and air-fuel ratio feedback control means for performing feedback control of the air-fuel ratio of an intake air-fuel mixture in the internal combustion engine based on the output value of the electromotive force generated between the pair of said electrode members.

20. An air-fuel ratio control apparatus in an internal combustion engine as set forth in claim 19, wherein the air-fuel ratio feedback control means includes in the internal combustion engine a fuel injection valve and a control unit provided with a computer for performing increase or decrease control of the injection quantity of a fuel injected pulsatingly to the internal combustion engine from said fuel injection valve based on the output value of the electromotive force generated between the pair of said electrode members.

21. An air-fuel ratio control apparatus in an internal combustion engine as set forth in claim 20, wherein the fuel injection quantity Ti is a value computed according to the following equation:

$$Ti = Tp \times COEF \times LAMBDA + Ts$$

wherein Tp stands for the basic injection quantity represented by the equation of $Tp = K \times Q/N$ in which K is a constant, Q stands for quantity of the air sucked in the internal combustion engine and N stands for an engine rotation number, COEF stands for various correction constants determined according to factors of engine driving states, LAMBDA stands for a feedback correction coefficient determined based on the output signal from the oxygen gas concentration-detecting apparatus, and Ts stands for a voltage correction value of a battery voltage.

* * * * *